(12) United States Patent
Leeflang et al.

(10) Patent No.: US 11,478,129 B2
(45) Date of Patent: Oct. 25, 2022

(54) APPARATUS, SYSTEMS, AND METHODS FOR EPICARDIAL IMAGING AND INJECTION

(71) Applicants: Stephen A. Leeflang, Sandy, UT (US); Christian S. Eversull, Palo Alto, CA (US)

(72) Inventors: Stephen A. Leeflang, Sandy, UT (US); Christian S. Eversull, Palo Alto, CA (US)

( * ) Notice: Subject to any disclaimer, the term of this patent is extended or adjusted under 35 U.S.C. 154(b) by 23 days.

(21) Appl. No.: 16/877,361

(22) Filed: May 18, 2020

(65) Prior Publication Data

US 2020/0275825 A1    Sep. 3, 2020

Related U.S. Application Data

(63) Continuation of application No. 14/542,545, filed on Nov. 15, 2014, now Pat. No. 10,653,297, which is a
(Continued)

(51) Int. Cl.
*A61B 1/00* (2006.01)
*A61B 17/34* (2006.01)
*A61B 1/05* (2006.01)
*A61B 1/015* (2006.01)
(Continued)

(52) U.S. Cl.
CPC ...... *A61B 1/00096* (2013.01); *A61B 1/00082* (2013.01); *A61B 1/00087* (2013.01);
(Continued)

(58) Field of Classification Search
CPC ............ A61B 1/00096; A61B 1/00082; A61B 1/00087; A61B 1/00098; A61B 1/00133; A61B 1/0125; A61B 1/015; A61B 1/018; A61B 1/05; A61B 1/0676; A61B 1/0684; A61B 1/313; A61B 17/00234; A61B 17/3403; A61B 17/3478; A61B 2017/0034; A61B 2017/3409
See application file for complete search history.

(56) References Cited

U.S. PATENT DOCUMENTS 6,379,319 B1 *  4/2002  Garibotto ............... A61B 17/11
                                                    600/585
6,447,444 B1 *  9/2002  Avni ..................... A61B 1/0005
                                                    600/121
(Continued)

*Primary Examiner* — Alexandra L Newton
*Assistant Examiner* — Rynae E Boler
(74) *Attorney, Agent, or Firm* — William A. English; Vista IP Law Group LLP

(57) ABSTRACT

Systems and methods are provided for injecting one or more agents into tissue within a patient's body that includes a catheter. A needle guide extends from a distal end of the catheter and terminates at a distal tip, e.g., including a foot with an atraumatic contact surface, the needle guide having a cross-section smaller than the distal end and being biased to a curved shape. The needle guide includes a passage communicating from a lumen of the catheter to an outlet at the distal tip, and a needle device is disposed within the passage that may be deployed from the outlet to inject one or more agents into tissue. The catheter also includes an imaging assembly on the distal end configured to acquire images of tissue adjacent the needle guide distal tip.

21 Claims, 10 Drawing Sheets

Related U.S. Application Data continuation of application No. PCT/US2014/065846, filed on Nov. 14, 2014.

(60) Provisional application No. 62/066,916, filed on Oct. 22, 2014, provisional application No. 61/983,556, filed on Apr. 24, 2014, provisional application No. 61/981,870, filed on Apr. 21, 2014, provisional application No. 61/935,908, filed on Feb. 5, 2014, provisional application No. 61/904,011, filed on Nov. 14, 2013.

(51) Int. Cl.
*A61B 1/06* (2006.01)
*A61B 1/012* (2006.01)
*A61B 1/018* (2006.01)
*A61B 1/313* (2006.01)
*A61B 17/00* (2006.01)

(52) U.S. Cl.
CPC ...... *A61B 1/00098* (2013.01); *A61B 1/00133* (2013.01); *A61B 1/015* (2013.01); *A61B 1/018* (2013.01); *A61B 1/0125* (2013.01); *A61B 1/05* (2013.01); *A61B 1/0676* (2013.01); *A61B 1/0684* (2013.01); *A61B 1/313* (2013.01); *A61B 17/00234* (2013.01); *A61B 17/3403* (2013.01); *A61B 17/3478* (2013.01); *A61B 2017/0034* (2013.01); *A61B 2017/3409* (2013.01)

(56) References Cited

U.S. PATENT DOCUMENTS

| | | | | |
|---|---|---|---|---|
| 8,221,310 B2* | 7/2012 | Saadat | ................. | A61B 5/6882 |
| | | | | 600/129 |
| 8,591,402 B2* | 11/2013 | Yamakita | ........... | A61B 1/00089 |
| | | | | 600/127 |
| 2005/0228452 A1* | 10/2005 | Mourlas | ........... | A61M 25/0138 |
| | | | | 607/3 |
| 2007/0083217 A1* | 4/2007 | Eversull | ................. | A61B 1/053 |
| | | | | 606/114 |
| 2012/0323069 A1* | 12/2012 | Stout | ..................... | A61B 1/303 |
| | | | | 600/104 |

\* cited by examiner

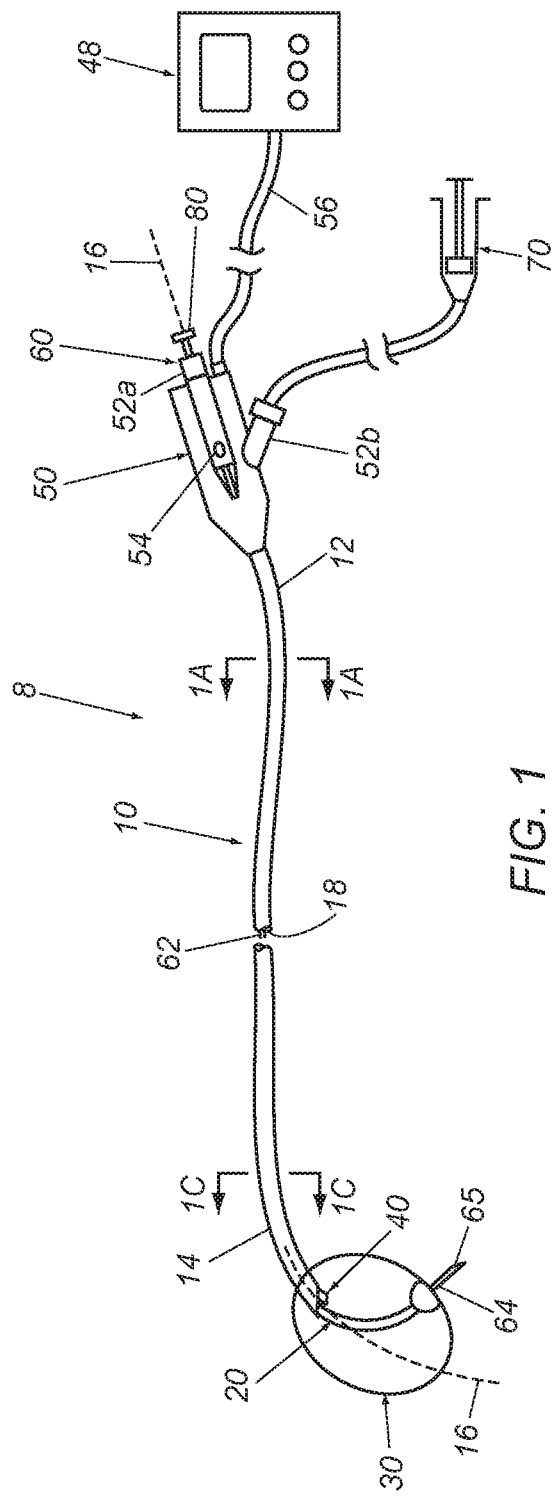
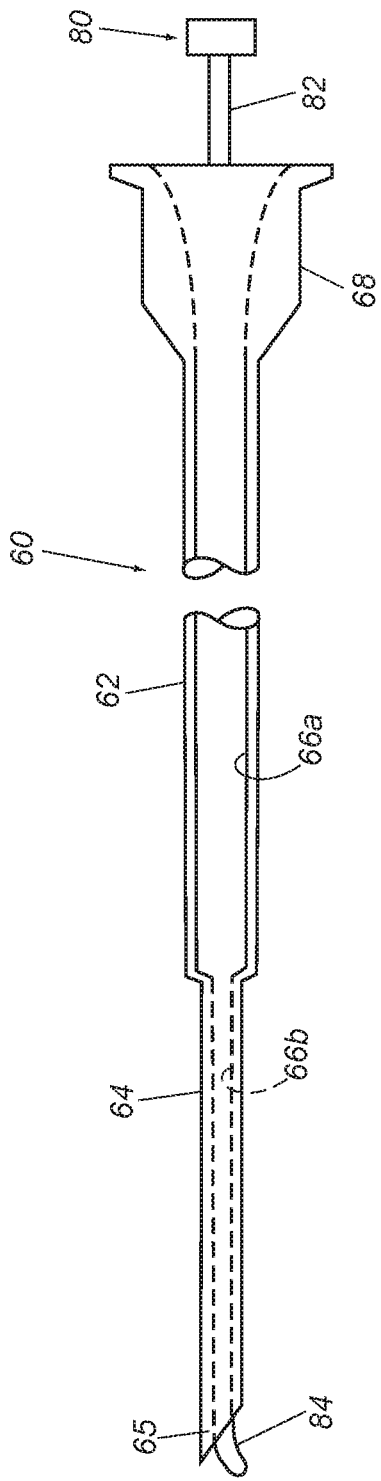
FIG. 1
FIG. 2

APPARATUS, SYSTEMS, AND METHODS FOR EPICARDIAL IMAGING AND INJECTION

RELATED APPLICATION DATA

This application is a continuation of co-pending application Ser. No. 14/542,545, filed Nov. 15, 2014, issuing as U.S. Pat. No. 10,653,297, which is a continuation of International Application No. PCT/US2014/065846, filed Nov. 14, 2014, which claims benefit of provisional application Ser. Nos. 61/904,011, filed Nov. 14, 2013, 61/935,908, filed Feb. 5, 2014, 61/981,870, filed Apr. 21, 2014, 61/983,556, filed Apr. 24, 2014, and 62/066,916, filed Oct. 22, 2014, the entire disclosures of which are expressly incorporated by reference herein.

FIELD OF THE INVENTION

The present invention relates generally to apparatus, systems, and methods for imaging and/or performing medical procedures, and more particularly to apparatus, systems, and methods for injecting one or more agents into tissue, e.g., into the of a patient's heart epicardially.

BACKGROUND

The pericardial space provides an advantageous approach for many medical procedures. For some procedures, an epicardial approach may provide more direct access with fewer risks, such as the risk of clotting or other embolic events (e.g., release of device debris, air, and the like), e.g., as compared to endovascular approaches. Recently, there has been a large increase in the number of therapies designed to access and treat the heart via an epicardial approach—both via a subxyphoid access as well as surgical access. Many of these treatments require careful positioning, e.g., to target specific areas as well as to avoid other specific areas. These areas can include atrial appendages, coronary arteries, coronary veins, fat pads, separate/individual chambers of the heart and/or walls thereof, and the like. These anatomies are difficult to visualize in general using standard imaging modalities, such as fluoroscopy or ultrasound, where resolution is poor and/or the ability to deliver and contain contrast is difficult, which may present a real and significant challenge to the development of truly therapeutic devices and procedures.

Therefore, apparatus and methods that facilitate medical procedures via epicardial approach would be useful.

SUMMARY

The present invention is directed to apparatus, systems, and methods for performing medical procedures, e.g., within the pericardial space of a patient's body. More particularly, the present invention is directed to apparatus, systems, and methods for imaging and/or injecting one or more agents into tissue, e.g., into the wall of a patient's heart epicardially.

A device with the ability to easily navigate epicardially via direct visualization and deliver a range of treatments to a range of anatomy(s) is highly desirable. For example, an injection catheter needs to avoid major coronary arteries and veins. An ablation system needs to be positioned reliably and ensure good apposition with the tissue in addition to avoiding certain anatomies. An atrial appendage closing device needs to ensure proper positioning and safe closure. All of these objectives may be more easily accomplished with apparatus and systems that provide direct visualization.

In accordance with one embodiment, an apparatus is provided for imaging tissue during a medical procedure that includes a tubular member including a proximal end, a distal end sized for introduction into a patient's body, and one or more lumens extending between the proximal and distal ends. A tubular extension extends distally beyond the distal end to a distal tip, the tubular extension having a cross-section smaller than the distal end and being biased to a curved shape, the tubular extension including a passage communicating from a first lumen of the tubular member to an outlet at the distal tip. The apparatus may also include a foot on the distal tip including a substantially atraumatic contact surface having an area larger than the cross-section of the tubular extension for contacting tissue; and an imaging assembly on the distal end configured to acquire images of tissue adjacent the foot.

In accordance with another embodiment, an apparatus is provided for imaging tissue during a medical procedure that includes a tubular member including a proximal end, a distal end sized for introduction into a patient's body, and one or more lumens extending between the proximal and distal ends. A tubular extension extends distally beyond the distal end to a distal tip, the tubular extension having a cross-section smaller than the distal end and being biased to a curved shape, the tubular extension including a passage communicating from a first lumen of the tubular member to an outlet at the distal tip. The apparatus may also include a foot on the distal tip including a substantially atraumatic contact surface having an area larger than the cross-section of the tubular extension for contacting tissue; a substantially transparent expandable member comprising a proximal end attached to the tubular member distal end and a distal end attached to one of the distal tip and the foot; and an imaging assembly on the distal end within an interior of the expandable member and configured to acquire images of tissue adjacent the foot and the expandable member surface surrounding the foot.

In accordance with still another embodiment, a system is provided for injecting one or more agents into tissue within a patient's body that includes a catheter including a tubular member comprising a proximal end, a distal end sized for introduction into a patient's body, and one or more lumens extending between the proximal and distal ends; a needle guide extending distally beyond the distal end to a distal tip, the needle guide having a cross-section smaller than the distal end and being biased to a curved shape, the needle guide including a passage communicating from a first lumen of the tubular member to an outlet at the distal tip; and an imaging assembly on the distal end configured to acquire images of tissue adjacent the needle guide distal tip. The system also includes a needle device including a needle tip within the passage of the needle guide and movable from a retracted position wherein the needle tip is disposed within the passage and an advanced position wherein the needle tip is deployed from the outlet.

In accordance with another embodiment, a method is provided for imaging tissue structures within a patient's body, comprising introducing a distal end of a catheter into a pericardial space adjacent the patient's heart; deploying a curved delivery guide extending from the distal end of the catheter such that a foot on the delivery guide is oriented transversely relative to the distal end; manipulating the catheter such the foot contacts the heart wall; and acquiring one or more images of the foot and adjacent tissue to identify a target location on the heart wall.

In accordance with still another embodiment, a method is provided for imaging tissue structures within a patient's body, comprising introducing a distal end of a catheter into a patient's body; expanding a balloon on the distal end wherein a curved delivery guide extends from the distal end of the catheter through an interior of the balloon, the delivery guide comprising a foot coupled to a distal surface of the balloon such that the foot is oriented transversely relative to the distal end; manipulating the catheter such the foot and balloon contact tissue within the patient's body; and acquiring one or more images of the foot and adjacent tissue to identify a target location within the patient's body.

In accordance with yet another embodiment, a method is provided for injecting one or more agents into a patient's heart. The method includes introducing a distal end of a catheter into a pericardial space adjacent the patient's heart; deploying a curved needle guide extending from the distal end of the catheter such that a foot on the needle guide is oriented transversely relative to the distal end; manipulating the catheter such the foot contacts the heart wall; acquiring one or more images of the foot and adjacent tissue to identify a target location on the heart wall; and deploying a needle device from the needle guide into the target location to deliver one or more agents.

Other aspects and features of the present invention will become apparent from consideration of the following description taken in conjunction with the accompanying drawings.

BRIEF DESCRIPTION OF THE DRAWINGS

The drawings illustrate exemplary embodiments of the invention, in which:

FIG. 1 is a side view of an exemplary embodiment of a system for performing injections including a catheter with a curved delivery guide and imaging assembly, and a needle device deployable from the delivery guide.

FIG. 2 is a partial cross-sectional side view of an exemplary embodiment of a needle device that may be included in the system of FIG. 1.

DETAILED DESCRIPTION OF THE EXEMPLARY EMBODIMENTS

Figure 7:
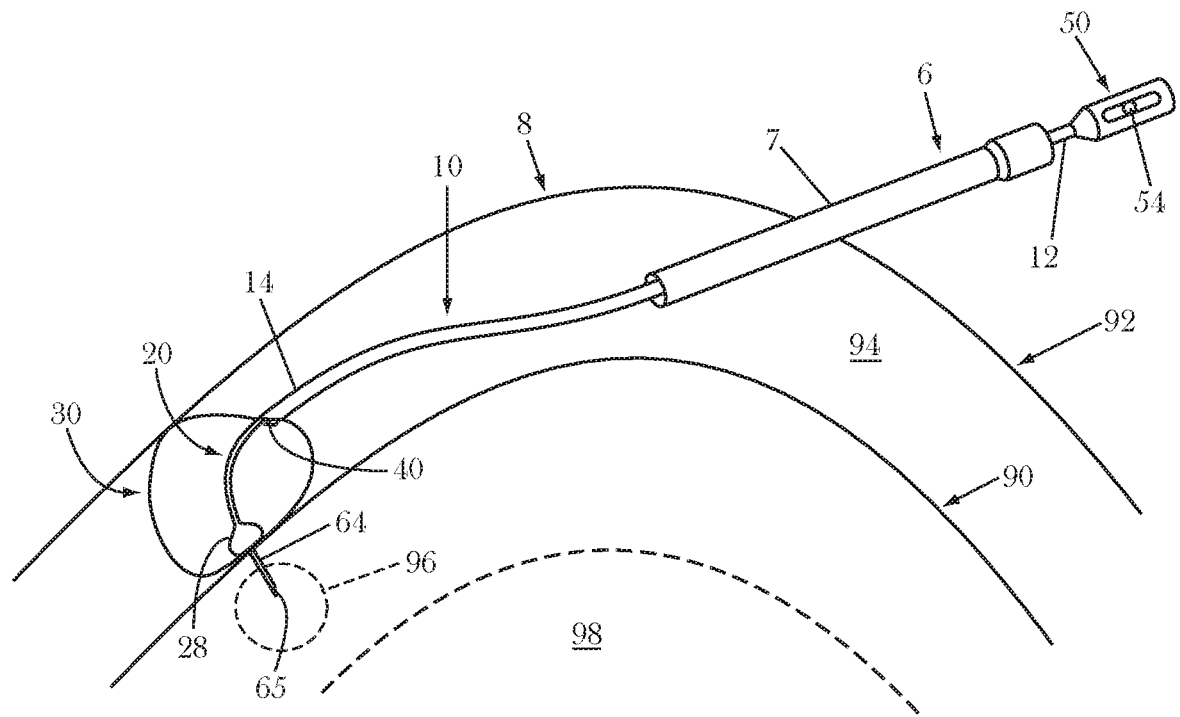
FIG. 7 is a cross-sectional view of a patient's body showing an exemplary method for using the system of FIG. 1 to inject one or more agents into the epicardium of the patient's heart.

Turning to the drawings, FIG. 1 shows an exemplary embodiment of a system 8 for performing a medical procedure within a patient's body, e.g., for imaging within the patient's body and/or injecting one or more agents into one or more tissues or lumens, e.g., into the wall of a patient's heart (not shown, see, e.g., FIG. 7). As shown, the system 8 generally includes an imaging and/or delivery catheter 10 carrying a needle or delivery guide 20, a balloon 30, and an imaging assembly 40, and a needle device 60 deployable from the delivery guide 20. Optionally, the system 8 may include one or more additional components or devices, e.g., an access or delivery sheath, one or more stylets, one or more additional needle devices, and/or one or more guidewires or rails (all not shown). In addition or alternatively, the catheter 10 may be used to introduce other devices, e.g., a laser device, an electrical energy ablation device, and the like (not shown), instead of or in addition to the needle device 60, as described elsewhere herein.

Generally, the catheter 10 is an elongate tubular member including a proximal end 12, a distal end 14 sized for insertion into a patient's body, a central longitudinal axis 16 extending between the proximal and distal ends 12, 14, and one or more lumens 18 extending between the proximal and distal ends 12, 14. The needle or delivery guide 20, a balloon 30, and an imaging assembly 40 may be provided on the distal end 14, e.g., to facilitate imaging the patient's body and/or deploying a tip 65 of the needle device 60 to inject one or more agents and/or otherwise perform a medical procedure, as described elsewhere herein.

In exemplary embodiments, as shown in FIGS. 1A-1D, the catheter 10 may include a central or primary lumen 18a and one or more auxiliary lumens 18b-18c that extend at least partially between the proximal and distal end 12, 14, e.g., within different sections of the catheter 10, as described further elsewhere herein. In one embodiment, shown in FIG. 1A, a proximal section of the catheter 10 may include a single relatively large central lumen 18a, which may extend from the proximal end 12 to a location adjacent the distal end 14. The central lumen 18a may include one or more tubes, wires, and/or other components extending between the proximal and distal ends 12, 14 of the catheter 10. For example, as shown, the central lumen 18a may include an inflation lumen 39 communicating with an interior of the balloon 30, a delivery lumen 69 for receiving the needle device 60, and one or more cables 49 for providing power to the imaging assembly 40 and/or for providing images output from the imaging assembly 40. Optionally, one or more pull wires (one pull wire 19 shown) and/or stylets (not shown) may be provided within the central lumen 18a, e.g., if the distal end 14 of the catheter 10 is steerable and/or otherwise deflectable.

Figure 1A:
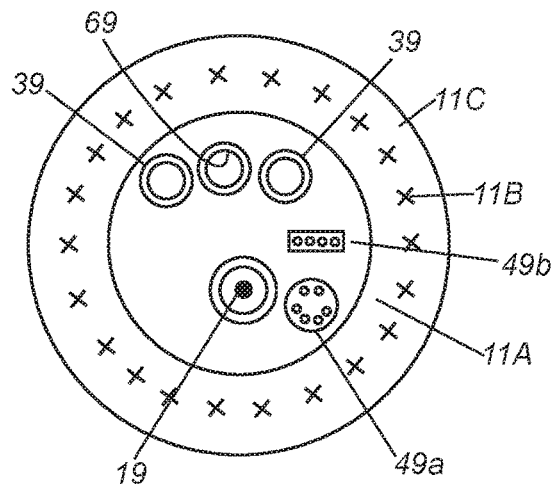
FIGS. 1A and 1B are cross-sectional views of the catheter of FIG. 1 taken along line 1A-1A, showing alternative exemplary lumen configurations for a proximal section of the catheter.
Figure 1B:
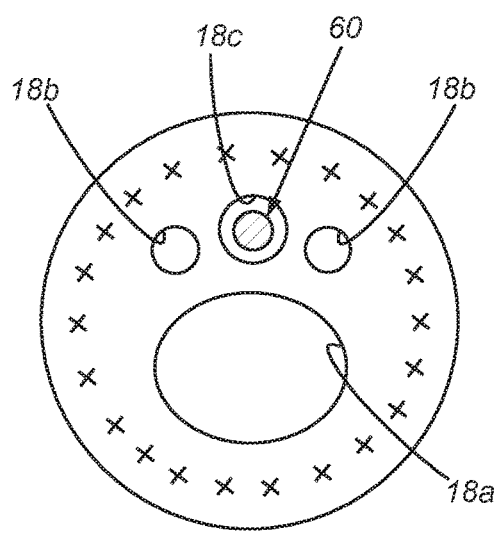
Figure 1C:
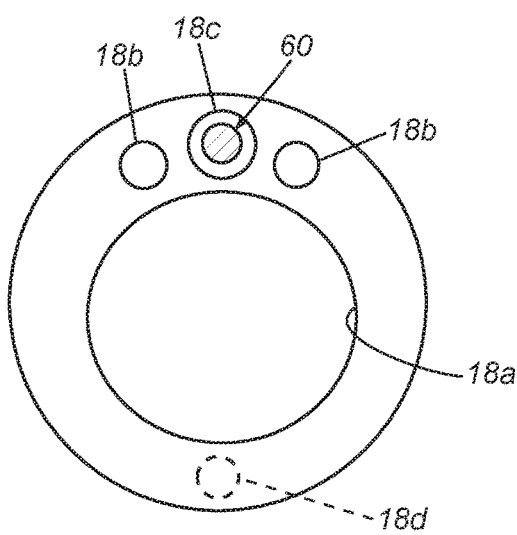
FIGS. 1C and 1D are cross-sectional views of the catheter of FIG. 1 taken along line 1C-1C, showing alternative exemplary lumen configurations for a distal section of the catheter.
Figure 1D:
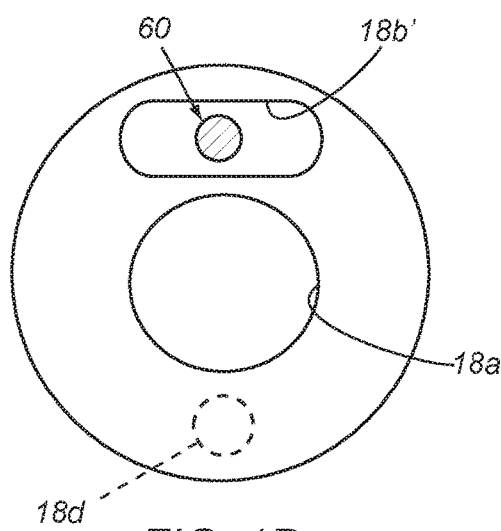

As shown in FIGS. 1C and 1D, within a distal section of the catheter 10 adjacent the distal end 14, the configuration of the lumens 18 may optionally change to provide different mechanical properties and/or other characteristics for the distal section, e.g., to provide one or more auxiliary lumens 18b-18d for receiving one or more of the components within the central lumen 18a within the proximal section. For example, one or more inflation lumens 18b (two shown) may be provided in the wall of the catheter 10 that communicate with the inflation lumen(s) 39 in the proximal section and/or a delivery lumen 18c may be provided in the wall of the catheter 10 that communicates with the delivery lumen 69 that receives the needle device 60. Alternatively, as shown in FIG. 1D, a single auxiliary lumen 18b' may be provided in the distal section that is sized to receive the needle device 60 and allow inflation media to be introduced and/or removed around the needle device 60. In a further alternative, as shown in FIG. 1B, the auxiliary lumens 18b-18c may extend from the proximal end 12 to the distal end 14 of the catheter 10.

Optionally, as shown in FIGS. 1C and 1D, one or more additional lumens 18d (one shown in phantom) may be provided for receiving a stylet and/or pull wire (not shown). In addition or alternatively, if desired an infusion/aspiration lumen may be provided, e.g., communicating with one or more ports (not shown) on the distal end 14 adjacent the balloon 30. Such a lumen and port(s) may allow infusion of saline or other transparent fluids to clear the field around the balloon 30 of blood or other obstructive materials and/or may allow aspiration to remove such materials, blood, and/or other materials, e.g., that have accumulated in the pericardial space.

Optionally, the distal end 14 may include one or more features to enhance visibility under ultrasound, Mill or other imaging modalities, e.g., by providing one or more radiopaque markers on and/or doping one or more regions of the distal end 14, the delivery guide 20, the foot 28, and/or the balloon 30, e.g. as known in the art.

The catheter 10 may be substantially flexible, semi-rigid, and/or rigid along its length, and may be formed from a variety of materials, including plastic, metal, and/or composite materials, as is well known to those skilled in the art. For example, the catheter 10 may be substantially flexible at the distal end 14 to facilitate advancement through tortuous anatomy, and/or may be semi-rigid or rigid at the proximal end 11 to enhance pushability and/or torqueability of the catheter 10 without substantial risk of buckling or kinking. In an exemplary embodiment, with particular reference to FIGS. 1A-1D, the catheter 10 may include an inner liner 11A, e.g., at least partially or entirely surrounding or otherwise defining the central lumen 18a, a reinforcement layer 11B surrounding the inner liner 40, and an outer jacket 11C surrounding the reinforcement layer 42, each of which may extend at least partially between the proximal and distal ends 12, 14 of the catheter 10. The reinforcement layer 11B and/or outer jacket 11C may be attached to the inner liner 11A, e.g., by laminating, adhering, adhesive bonding, ultrasonic welding, reflowing or other heating, and the like. In an exemplary embodiment, the central lumen 18a and/or one or more of the auxiliary lumens 18b-18d may include lubricious material or may be formed from one or more layers of thermoplastic or other polymeric material including one or more coatings on the inner surface 41a having desired properties, e.g., a hydrophilic and/or lubricious coating, e.g., similar to the liners disclosed in U.S. Pat. Nos. 7,550,053 and 7,553,387, and U.S. Publication No. 2009/0126862, the disclosures of which are expressly incorporated by reference herein.

Optionally, any or all of the inner liner 11A, reinforcement layer 11B, and/or outer jacket 11C may be formed from multiple layers of like or different materials (not shown), e.g., to provide desired material properties in the different sections of the catheter 10. In an exemplary embodiment, the outer jacket 1C may be formed from PEBAX, nylon, urethane, and/or other thermoplastic material, e.g., such that the material of the outer jacket 11C may be heated and reflowed and/or otherwise formed around the components.

Optionally, a distal section of the catheter 10 may be pre-shaped, steerable or deflectable, i.e., may be bent, curved, or otherwise deflected. For example, in the embodiment shown in FIG. 1, the distal end 14 may be biased to a curved shape, e.g., having a radius of curvature larger than the delivery guide 20. Optionally, a stylet (not shown) may be inserted into the catheter 10 (e.g., into stylet lumen 18d shown in FIGS. 1C and 1D, e.g., to straighten the distal end 14 and/or otherwise support the distal end 14 during introduction into a patient's body. Alternatively, the catheter 10 may include one or more pull wires 19, as shown in FIG. 1A, which may be actuated to direct the distal end 14 between straightened and curved shapes, as desired during use.

Returning to FIG. 1, a handle or hub 50 may be provided on the proximal end 12 of the catheter 10, e.g., configured and/or sized for holding and/or manipulating the system 8 from the proximal end 12. In addition, the handle 50 may include one or more ports 52 communicating with respective lumens within the catheter 10. For example, port 52a may communicate with delivery lumen 69, 18c, or 18b' e.g., for removably receiving the needle device 60 therein, as described further elsewhere herein. Optionally, the port 52a include one or more valves, e.g., a hemostatic valve (also not shown), which may provide a substantially fluid-tight seal, while accommodating insertion of the needle device 60 (or other device) into the delivery lumen 69, 18c, or 18b.' Alternatively, the needle device 60 may be integrally formed as part of the catheter 10, i.e. not removable, and the port 52a may be omitted.

In addition, a side port 52b may be provided that communicates with the inflation lumen(s) 39, 18b, e.g., for delivering fluid into and/or aspirating fluid from the interior 36 of the balloon 30, as described elsewhere herein. For example, as shown in FIG. 1, a syringe or other source of inflation media 70 may be coupled to the side port 52b for introducing and/or removing fluid, e.g., saline, nitrogen, and the like, into and/or from the interior 36 of the balloon 30.

The handle 50 and/or proximal end 12 may also include one or more connectors, e.g., electrical connectors, and the like (not shown), for connecting the imaging assembly 40 to a controller 48, e.g., including a power source, processor, display, and the like (not shown), via one or more cables 56.

Finally, the handle 50 may also include one or more actuators, such as sliders, buttons, switches, rotational actuators, locks, and the like, e.g., for activating and/or manipulating components on the distal end 14 or otherwise operating the apparatus 10. For example, an actuator 54 may be provided that is coupled to the needle device 60 for deploying and retracting the needle tip 65 during an injection and/or a locking mechanism (not shown) may be included for locking the needle device 60 in one or more predetermined positions, as described further elsewhere herein. In addition, one or more switches 49 may be provided on the controller 48 and/or on the handle 50 for operating the imaging assembly 40, also as described further elsewhere herein. If the catheter 10 is steerable or deflectable, one or more sliders or other actuators (not shown) may also be provided for directing respective pull wire(s) to deflect the distal end 14, or a port (not shown) may be provided for receiving a stylet, e.g., to straighten or otherwise deflect the distal end 14, as described elsewhere herein.

Figure 3:
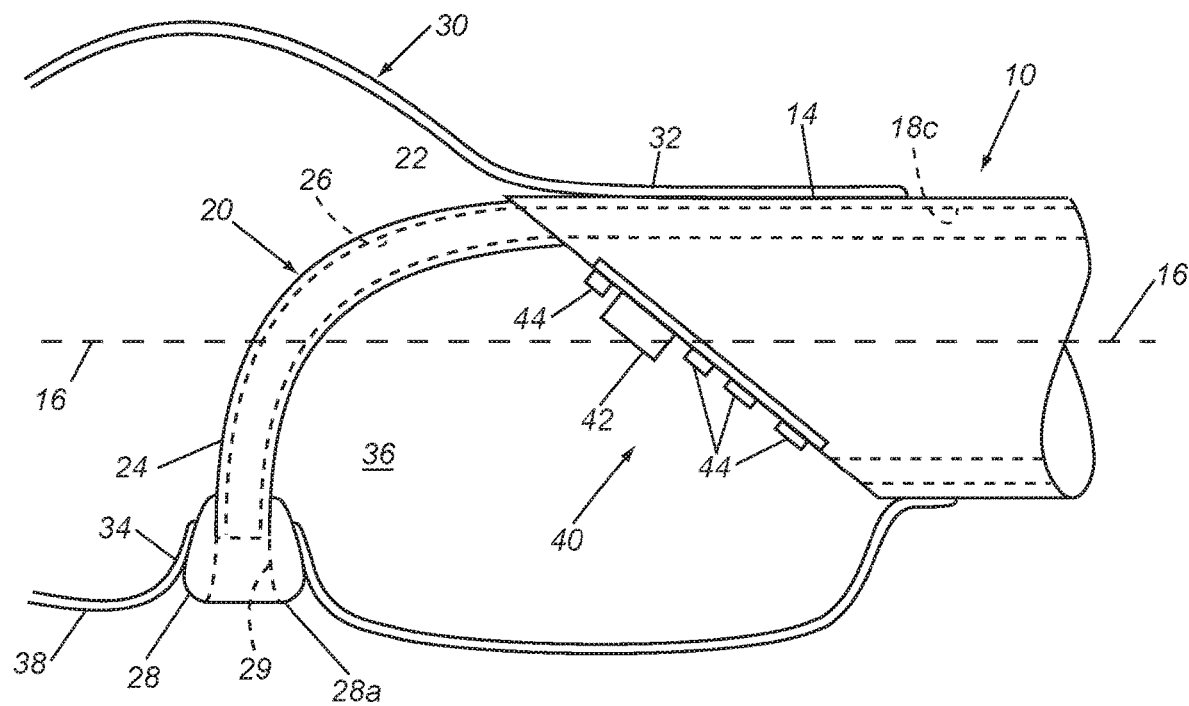
FIG. 3 is a side view of a distal end of the catheter of FIG. 1, showing an exemplary embodiment of the delivery guide and an imaging assembly within a balloon on the distal end.

Turning to FIG. 3, the distal end 14 of the catheter 10 is shown, providing additional detail of the components carried thereon. For example, as shown, the delivery guide 20 may include a tubular member biased to a curved shape and yet sufficiently flexible to be directed to a substantially straightened shape (not shown), e.g., to facilitate introduction into a patient's body, as described elsewhere herein.

The delivery guide 20 generally includes a proximal end 22 attached to the distal end 14 of the catheter 10, a distal end 24 terminating in a foot 28, and a lumen or passage 26 extending between the proximal and distal ends 22, 24. The passage 26 may communicate between the delivery lumen 18c, 69 in the catheter 10 and an outlet 29 in the foot 28, and/or may be sized to receive at least the tip 65 of the needle device 60. As shown, the delivery guide 20 has a smaller outer diameter or other maximum cross-section than the distal end 14 of the catheter 10 and is mounted offset from the central axis 16 of the catheter 10. For example, attaching the delivering guide 20 eccentrically to the catheter 10 opposite the imaging assembly 40 may minimize the extent that the delivery guide 20 obstructs the field of view of the imaging assembly 40, as described elsewhere herein.

The proximal end 22 of the delivery guide 20 may be attached to the distal end 14 of the catheter 10 using known methods. In exemplary embodiments, the proximal end 22 of the delivery guide 20 may be may be butted against the distal end 14, at least partially received in a recess (not shown) in the distal end 14, received over a nipple (also not shown) on the distal end 14, and/or attached using other methods to substantially permanently mount the delivery guide 20 on the distal end 14 such that the passage 26 is aligned with the delivery lumen 18c, 69 of the catheter 10. In addition or alternatively, the delivery guide 20 may be bonded to the catheter 10, e.g., using an adhesive, heating, sonic welding, and the like.

The delivery guide 20 may be biased to a curved shape defining a simple uniform radius curve or may be biased to a more complicated curvilinear shape as desired, e.g., to place the foot 28 and outlet 29 at a desired location relative to the distal end 14 of the catheter 10. For example, it may be desirable to orient the outlet 29 substantially perpendicular to the longitudinal axis 16 of the catheter 10, e.g., to deploy the tip 65 of the needle 60 into the epicardium or other tissue structure along which the distal end 14 of the catheter 10 is disposed. In an exemplary embodiment, the delivery guide 20 may be formed from elastic material, e.g., Nitinol, to allow the delivery guide 20 to be straightened, e.g., to pass through an introducer or sheath, yet resiliently return to its curved shape while deflecting as needed to reduce the risk of damaging tissue contacted by the foot 28. In an alternative embodiment, the delivery guide 20 may be actuatable between curved and substantially straight shapes, e.g., using a stylet or pull wire (not shown), similar to that described for the distal end 14 of the catheter 10.

Figure 5A:
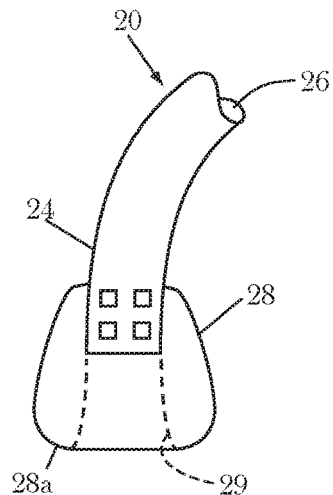
FIGS. 5A and 5B are details of an exemplary embodiment of a foot that may be provided on the delivery guide of a catheter, such as that shown in FIG. 1.
Figure 5B:
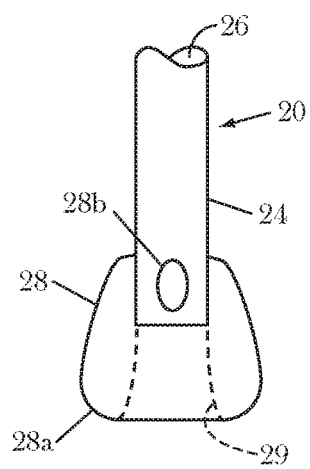
Figure 5C:
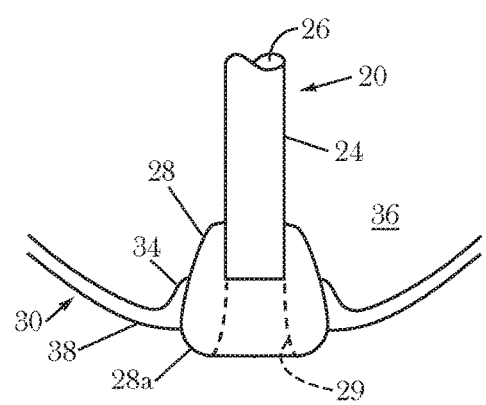
FIG. 5C is a detail of an exemplary embodiment of a foot and balloon of the catheter of FIG. 1.

Turning to FIGS. 5A-5C, the foot 28 may be attached to the distal end 24 of the delivery guide 20, e.g., to provide an enlarged and/or substantially atraumatic tip for the delivery guide 20. For example, as shown, the foot 28 may include a substantially atraumatic contact surface 28a having an area larger than the cross-section of the delivery guide 20, which may reduce the risk of puncturing, skiving, or otherwise damaging tissue contacted by the delivery guide 20. In an exemplary embodiment, the foot 28 may be molded or otherwise formed separately from the delivery guide and attached to the distal end 24, e.g., by one or more of an interference fit, melting, sonic welding, bonding with adhesive, and the like. FIG. 5A shows optional relief cuts that may be provided in distal end 24 of the delivery guide 20 or foot 28 to enhance attachment. Alternatively, the foot 28 may be molded or otherwise formed directly on the distal end 24. The foot 28 may be formed from a variety of materials, e.g., elastomeric materials, such as silicone, thermoplastic materials, such as urethanes, polyether block amide, nylons, fluoropolymers or thermoset materials, metals, and the like.

Optionally, as shown in FIG. 5B, a window 28b may be provided on the foot 28 and delivery guide 20 that may allow the lumen 26 of the delivery guide 20 to be viewed immediately adjacent the outlet 29. For example, the window 28b may allow a user to view the tip of the needle device 60 (not shown), e.g., to confirm that the tip is positioned immediately adjacent the outlet 29 before deployment (or when the needle device 60 is first loaded into the catheter 10), as described elsewhere herein. Alternatively, the foot 28 may be formed from substantially transparent or translucent material to allow the tip 65 of the needle device 60 to be visually identified adjacent the outlet 29. In addition or alternatively, the foot 28 may include one or more features (not shown) to facilitate identifying the foot 28 in images acquired by the imaging assembly 40 and/or using external imaging. In addition or alternatively, the foot 28 and/or delivery guide 20 may include markers to facilitate identifying variables such as needle depth during deployment of the tip 65.

Figure 5D:
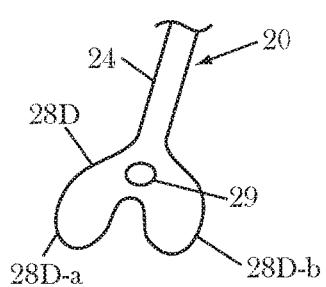
FIGS. 5D-5K are side views of alternative embodiments of a foot that may be provided on the delivery guide of a catheter, such as that shown in FIG. 1.
Figure 5E:
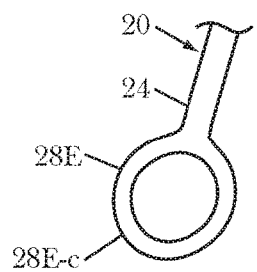
Figure 5F:
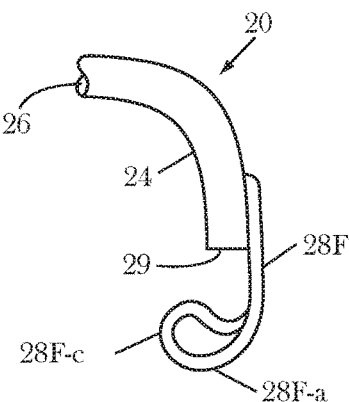
Figure 5G:
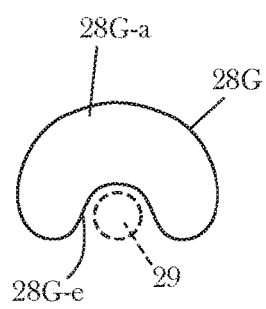
Figure 5H:
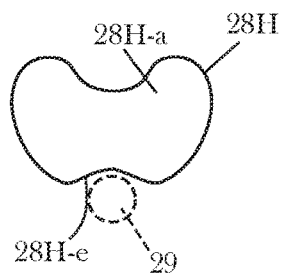
Figure 5I:
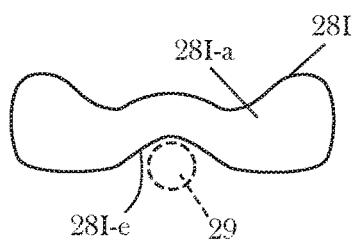

Turning to FIGS. 5D-5K, alternative embodiments are shown of a foot that may be provided instead of the foot 28 shown in FIGS. 5A-5C. For example, FIG. 5D shows a foot 28D that may include a recess 28D-b in the distal surface 28D-a, e.g., surrounding the outlet 29D, which may provide a working space into which one or more devices may be introduced to perform a procedure. FIG. 5E shows another embodiment of a foot 28E that includes a loop 28E-c extending from the distal end 24 of the delivery guide 20. FIG. 5F shows still another embodiment of a foot 28F that includes a loop 28F-c that is bent to define a distal contact surface 28F-a surrounding opening 28F-d aligned with the outlet 29 of the passage 26. FIGS. 5G-5I show end views of alternative shapes for a contact surface 28G-a, 28H-a, 28I-a of a foot 28G, 28H, 28I, e.g., including a recess 28G-e, 28H-e, 28I-e adjacent the outlet 29 of the passage 26.

Figure 5J:
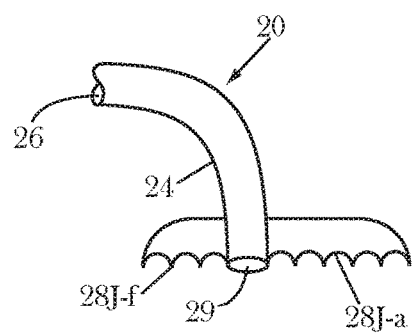
Figure 5K:
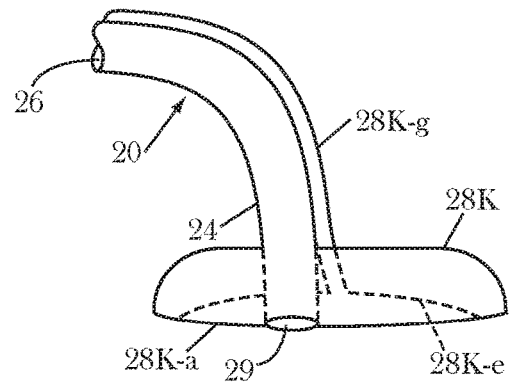

Turning to FIG. 5J, another exemplary embodiment of a foot 28J is shown that includes a substantially planar distal contact surface 28J-a that includes a plurality of engagement features 28J-f, e.g., barbs, treads, and the like, which may enhance engagement between the foot 28J and the tissue against which the foot 28J is placed. FIG. 5K shows another exemplary embodiment of a foot 28K that also includes a substantially planar distal contact surface 28K-a, which may optionally include one or more engagement features (not shown). In addition, the foot 28K includes a recess 28K-e in the contact surface 28K-a that communicates with a vacuum line 28K-g, e.g., extending along the delivery guide 20. A vacuum may be applied to the vacuum line to generate suction in the distal surface 28K-a to enhance engagement with contacted tissue. Such a vacuum feature and/or engagement features may enhance securing the foot 28J, 28K relative to the tissue such that any movement of the tissue (e.g., due beating of a patient's heart) causes corresponding movement to the foot 28J, 28K, the delivery guide 20, and potentially the balloon 30 and distal end 14 of the catheter 10 (not shown, see FIG. 1), which may stabilize the field of view of the imaging assembly 40. Thus, since the distal end 14 moves in synchronization with the tissue, the field of view may be relatively stationary, thereby stabilizing the images and facilitating identification of desired tissue structures. In a further alternative, one or more magnets may be provided on the foot (not shown), and a mating magnet may be positioned at a desired location within a chamber of the heart adjacent the foot, which may stabilize the foot relative to the heart. In a further alternative, a stabilizing element, e.g., the tip 65 of the needle device 60, may extend from the delivery guide 20 to engage and/or penetrate adjacent tissue, thereby eliminating or reducing relative motion between the imaging assembly 40 and tissue being imaged and thereby providing image stabilization.

Figure 6A:
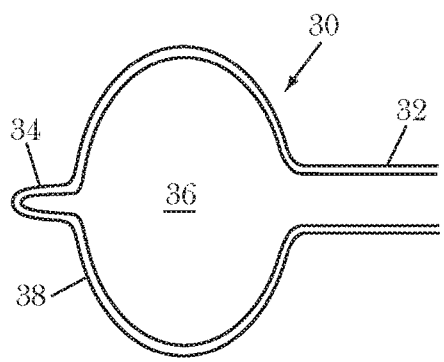
FIGS. 6A-6C are details showing an exemplary method for making a balloon for the catheter of FIG. 1.
Figure 6B:
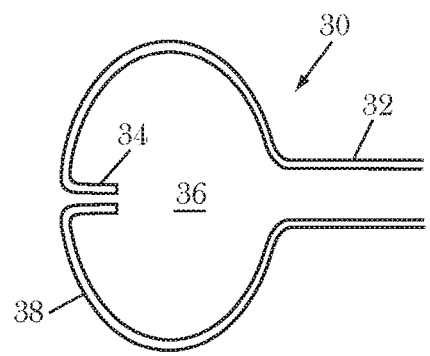
Figure 6C:
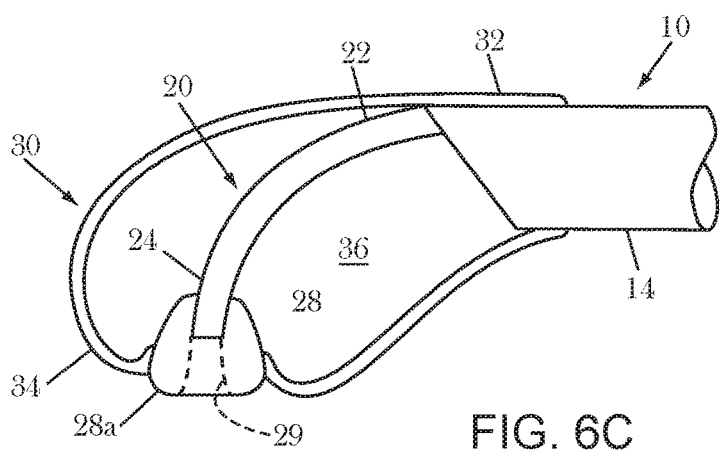

With additional reference to FIGS. 6A-6C, the balloon 30 may include a proximal end 32 attached to the distal end 14 of the catheter 10 and a distal end 34 attached to the distal end 24 of the delivery guide 20 and/or foot 28. FIG. 6A shows an exemplary shape of a balloon 30 that may be provided, e.g., after being dipped or otherwise formed.

As shown in FIG. 6C, the proximal end 32 of the balloon 30 may be secured to the outer surface of the catheter 10, e.g., using an adhesive, heating, an interference fit, an outer collar (not shown), and the like. As shown in FIGS. 5C, 6B, and 6C, the distal end 34 of the balloon 30 may be attached to the distal end 24 of the delivery guide 20 and/or foot 28, e.g., such that the distal end 34 of the balloon 30 at least partially inverts on itself. This may facilitate close contact between a distal surface 38 of the balloon 30 and a tissue surface being viewed (not shown) and/or minimize gaps around the foot 28, which may reduce optical distortion and/or facilitate clearing fluid from between the balloon 30 and the contacted tissue surface. In addition, this arrangement may prevent the foot 28 from extending substantially beyond the distal surface 38 of the balloon 30, e.g., such that a contact surface 28a of the foot 28 is substantially coextensive with the balloon distal surface 38.

The balloon 30 may be expandable from a contracted or delivery condition (not shown) to an enlarged condition when fluid is introduced into an interior 36 of the balloon 30, e.g., as shown in FIGS. 1 and 7. Optionally, the balloon 30 may be shaped such that, in the enlarged condition, the balloon 30 may define a substantially flat distal surface 38, which may facilitate imaging tissue structures beyond the balloon 30 using the imaging assembly 40.

In an exemplary embodiment, the balloon 30 may be formed from compliant and/or elastic materials, e.g., elastomeric materials such as silicone, latex, isoprene, and chronoprene. The compliance of the balloon 30 may facilitate clearing fluid between the distal surface 38 and/or may neutralize the bias of the delivery guide 20 during introduction, as described elsewhere herein. Alternatively, the balloon 30 may be formed from substantially noncompliant material, e.g., polytetrafluoroethylene (PTFE), expanded polytetrafluoroethylene (EPTFE), fluorinated ethylenepropylene (FEP), polyethylene teraphathalate (PET), urethane, olefins, and polyethylene (PE), such that the balloon 30 expands to a predetermined shape when fully inflated to the enlarged configuration.

The material may be sufficiently flexible and/or elastic such that the distal surface 38 may conform substantially to the shape of contacted tissue structures, e.g., the epicardium of a patient's heart, which may displace blood or other fluid from between the distal surface 38 and the contacted tissue to facilitate imaging through the balloon 30. In addition or alternatively, the balloon 30 may act as a tissue spacer with the distal surface 38 directing soft tissue, e.g., such as cardiac tissue and/or pericardium, which may deform easily, away from the imaging assembly 40. In addition, the combination of the balloon 30, delivery guide 20, and foot 28 may provide a substantially fixed imaging depth, perspective, and/or field of view in images acquired with the imaging assembly 40, e.g., due to the foot 28 stabilizing the distal end 14 relative to the contacted tissue, as described elsewhere herein.

The balloon 30 may also neutralize undesired rotation of the delivery guide 20 during use. For example, the curved shape of the delivery guide 20 defines a plane that may induce a bias for the catheter 10 to orient itself when positioned between tissue structures, e.g., between outer wall of a heart and the pericardium. However, to properly image the desired anatomy and to deliver therapy to a target location (e.g., using needle delivery), it is desired for the delivery guide 20 to be oriented partly or substantially orthogonally to the heart surface. The bias of the curved shape may prevent a stable positioning of the delivery guide 20 relative to the heart, but the balloon 30 may neutralize this bias when inflated, as the balloon 30 may create a substantially spherical or cylindrical shape for the distal end 14, which is substantially neutral in the axis of rotation.

The material may also be substantially transparent, i.e., allow light from the imaging assembly 40 to pass therethrough and/or be reflected off tissue or other structures beyond the distal surface 38 of the balloon 30 back to the imaging assembly 40, as described elsewhere herein. As used herein, "transparent" refers to any material and/or fluid that may permit sufficient light to pass therethrough in order to identify or otherwise visualize objects through the material and/or fluid. "Light" as used herein may refer to light radiation within the visible spectrum, but may also include other spectra, such as infrared ("IR") or ultraviolet ("UV") light.

Figure 3A:
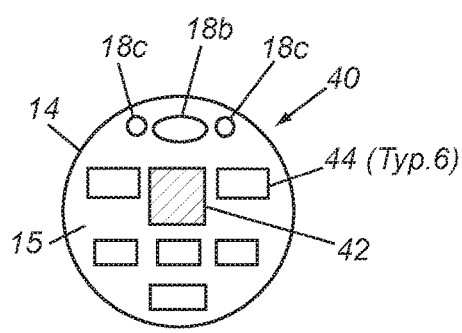
FIGS. 3A and 3B are details of the imaging assembly of FIG. 3.
Figure 3B:
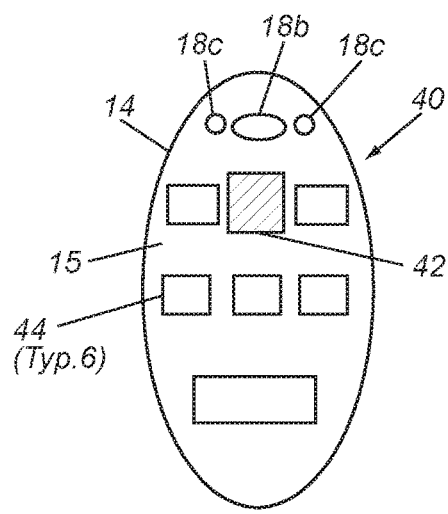

Returning to FIG. 3 and with additional reference to FIGS. 3A-3D, the imaging assembly 40 generally includes one or more cameras or other imaging elements 42 and one or more light sources 44, e.g., mounted on a distal surface 15 of the catheter 10. As best seen in FIG. 3, the distal end 14 of the catheter 10 may terminate in an angled distal surface 15, i.e., that is not perpendicular to the central axis 16 of the catheter, e.g., such that the distal surface 15 has a substantially circular shape when viewed along the central axis 16, as shown in FIG. 3A, and has an elliptical shape when viewed directly above (perpendicular to) the distal surface 15, as shown in FIG. 3B.

Figure 4A:
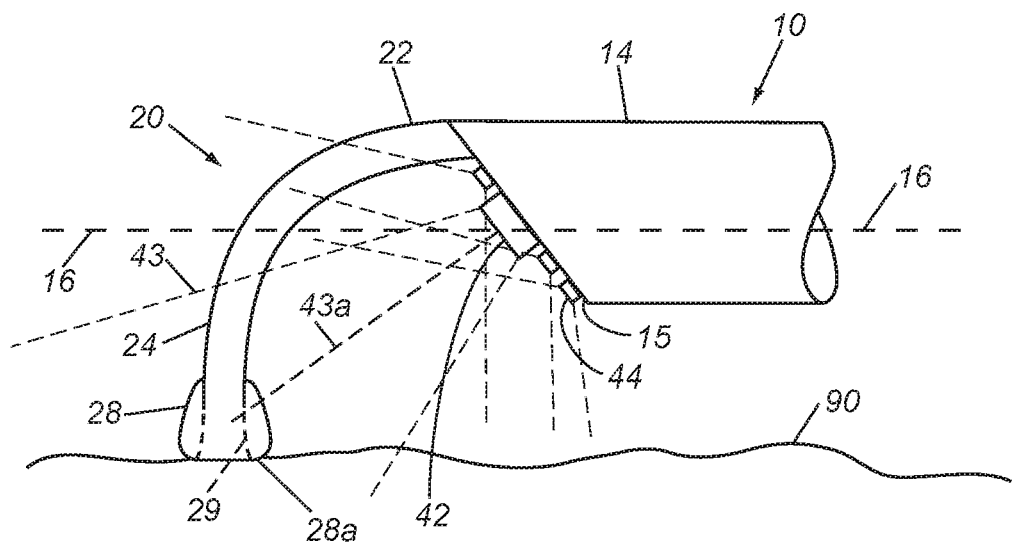
FIGS. 4A and 4B are details of the distal end of the catheter of FIG. 3 showing exemplary fields of view of the imaging assembly relative to the delivery guide and foot.
Figure 4B:
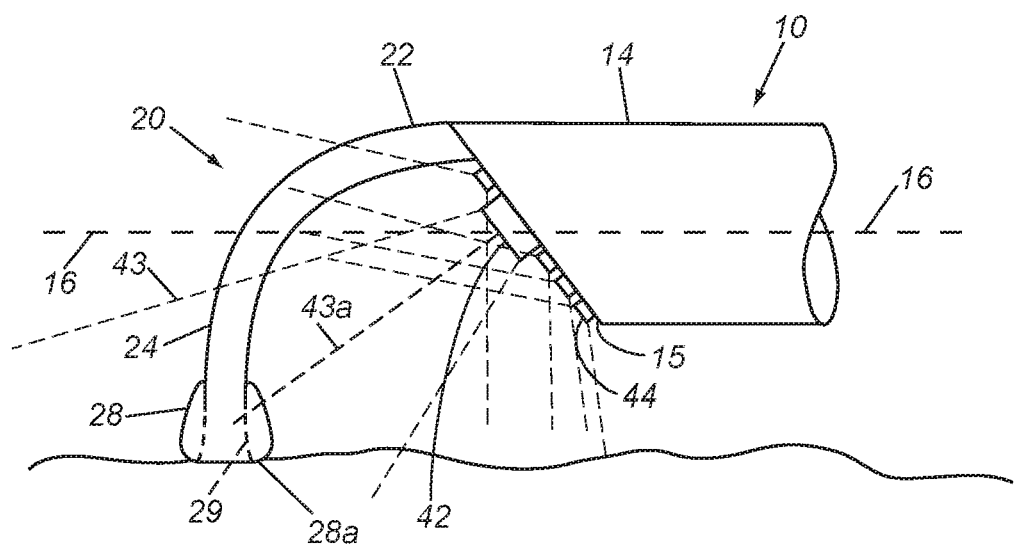

FIGS. 4A and 4B show exemplary fields of view that may be provided by the imaging element 42 and illumination fields that may be provided by the light sources 44. As shown, the imaging element 42 may have a field of view 43 that is angled relative to the distal end 14 of the catheter 10, i.e., such that a center axis 43a of the field of view 43 defines an angle, e.g., an acute angle, relative to the longitudinal axis 16 of the catheter 10. For example, with the delivery guide 20 in a relaxed, curved shape, the field of view 43 may be centered on the foot 28, which may facilitate imaging tissue contacted by the foot 28 (and the distal surface 38 of the balloon 30, not shown for clarity).

Similarly, the illumination fields 45 of the light sources 44 may also be angled relative to the distal end 14 of the catheter 10, e.g., to enhance illuminating tissue structures offset from the distal end 14. The illumination fields 45 of the light sources 44 may be substantially parallel to the field of view 43 or may be offset relative to one another, if desired. In addition, the illumination fields 45 may have a wider angle than the field of view 43, which may facilitate illumination and/or imaging of tissue and/or other features beyond the balloon 30.

In an exemplary embodiment, the imaging element 42 may include a CMOS (complementary metal-oxide-semiconductor) or CCD (charge-coupled device) sensor that is exposed within the interior 36 of the balloon 30 for capturing light images through the balloon 30. Alternatively, the imaging element 42 may include a bundle of optical fibers, e.g. a coherent image bundle, that extends between the proximal and distal ends 12, 14 of the catheter 10 and terminates adjacent the distal surface 15.

Optionally, one or more lenses, filters, and the like (not shown) may be coupled to the imaging element 42, e.g., to focus light from beyond the distal surface 38 of the balloon 30 onto the active area of the imaging element 42, direct a field of view of the imaging element 42, and/or filter undesired wavelengths of light, as known to those skilled in the art. Optionally, the imaging element 42 may be covered with a transparent protective coating, e.g., to prevent inflation media within the interior 36 from contacting the imaging element 42.

The one or more light sources 44 may include one or LEDs (light emitting diodes) and/or other light sources mounted on the distal surface 15 adjacent the imaging element 42, e.g., substantially surrounding the imaging element 42 to deliver light into the interior 36 and/or through the distal surface 38 of the balloon 30. Alternatively, one or more optical fibers may be provided that extend from the proximal end 12 of the catheter 10 to the distal surface 15, e.g., to emit light from a source in the controller 48 (shown in FIG. 1). The inflation media within the interior 36 may provide a heat sink, e.g., to dissipate any heat generated during operation by the light sources 44 and/or other chips or components mounted on the distal surface 15.

Figure 3C:
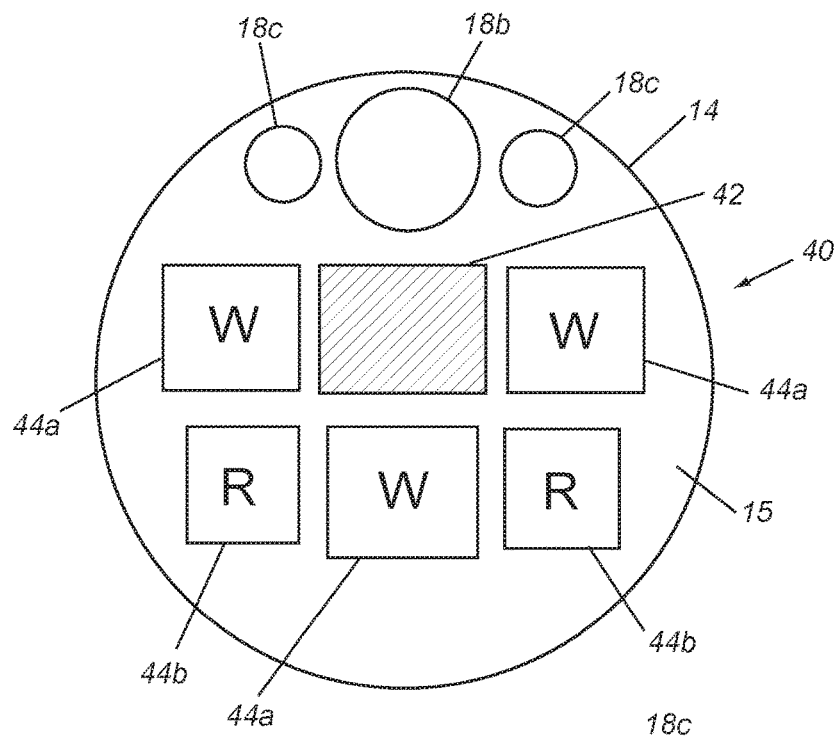
FIGS. 3C and 3D are details of alternative embodiments of the imaging assembly of FIG. 3.
Figure 3D:
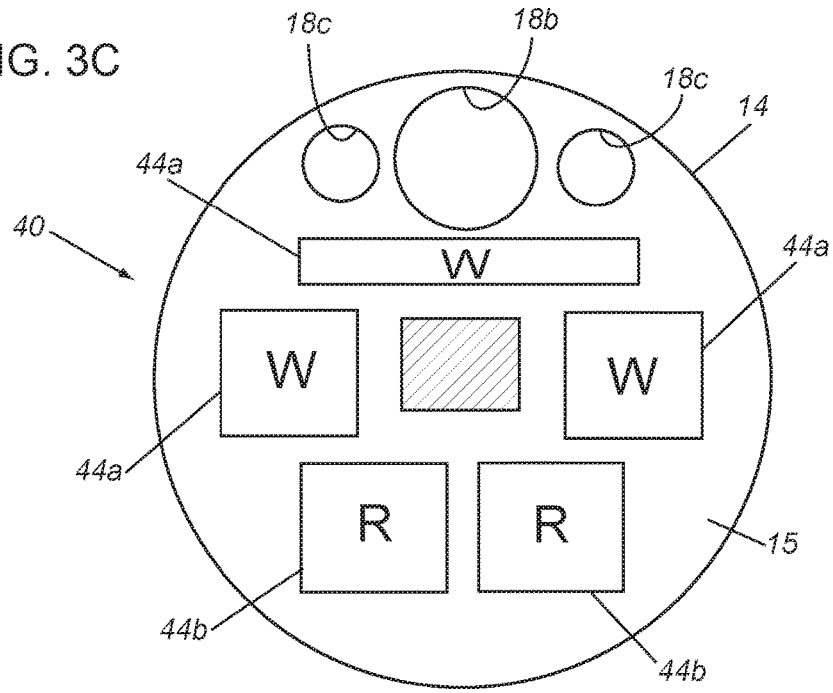

FIGS. 3C and 3D show exemplary configurations of light sources 44 that may be provided on the distal surface 15. For example, the light sources 44 may include a plurality of LEDs that emit visible white light and a plurality of LEDs that emit visible red light. Including additional light sources other than white may increase the bandwidth of light received by the imaging element 42 (for example, red light may make red tissues appear more natural in images). In addition or alternatively, the light sources 44 may be doped to increase the bandwidth emitted. Optionally, other sources of non-visible light, e.g., emitting infrared or ultraviolet light may be included, e.g., emitting longer wavelengths that may allow penetration into tissue to identify vessels below the tissue contact surface, such as vessels within the myocardium of a heart. The arrangement of the different color light sources may also adjust the depth of the field of view by placing different LEDs at different locations around imaging element 42. For example, as shown in FIG. 3D, the red LEDs 44b may be provided on the distal surface 15 closer to the foot 28 than the white LEDs 44a to place the red LEDs closer to tissue when the foot 28 is placed in contact with the tissue.

As shown in FIG. 1, the controller 48 may provide a power source for the imaging element 42 and/or light sources 44 and/or may receive image data from the imaging element 42, e.g., via cables 49a, 49b within the catheter 10 (shown in FIG. 1A) and cable 56. In addition, the controller 48 may include one or more processors, a display, memory, and the like (not shown) to process, display, and/or store the images acquired from the imaging element 42. For example, the imaging element 42 may acquire digital images and may convert the image data onboard to analog signals, which may be conveyed via the cables 49b, 56 to the controller 48, which may convert the images back to digital images and/or further process the images for display. Additional information on imaging assemblies and/or balloons that may be provided on the catheter 10 are disclosed in U.S. Pat. No. 6,979,290, the entire disclosure of which is expressly incorporated by reference herein.

Turning to FIG. 2, an exemplary embodiment of a needle device 60 is shown that may be loaded into the catheter 10, e.g., such that the tip 65 of the needle 60 may be deployed from and retracted into the delivery guide 20 (not shown, see FIG. 1), as described elsewhere herein. Generally, the needle device 60 includes a main portion 62, a tip portion 64, and a lumen 66 extending therebetween, e.g., from a hub 68 on the main portion 62 to the tip 65. The tip 65 may include a beveled, multi-faceted grind, or other sharpened shape, as desired to facilitate penetration into tissue. The hub 68 may include one or more connectors and/or seals (not shown), e.g., for coupling a source of one or more agents (also not shown) to the main portion 62 such that the agent(s) may be delivered through the lumen 66 and out the tip 65, e.g., into tissue within which the tip 65 is inserted.

Generally, the main portion 62 has a first outer diameter and length and the tip portion 64 has a second outer diameter and length, e.g., such that the main portion 62 may be received within the delivery lumen 69, 18c of the catheter 10 and the tip portion 64 may be received within the passage 26 of the delivery guide 20. In one embodiment, as shown in FIG. 2, the second outer diameter may be smaller than the first outer diameter and the second length may be shorter than the first length. The first length may be sufficiently long such that the main portion 62 extends from the proximal end 12 of the catheter 10 into a distal section of the catheter 10 adjacent the distal end 14, and the second length may be sufficient for the tip portion 64 to extend into the passage 26 and place the tip 65 adjacent the outlet 29. Thus, a transition 63 may be provided between the main portion 62 and the tip portion 64, e.g., within the distal section of the catheter 10 adjacent the distal end 14.

Similarly, the delivery lumen 69, 18c of the catheter 10 may include a first region defining a first inner diameter extending from the proximal end 12 to a location within the distal end 14 of the catheter, and a second region defining a second inner diameter smaller than the first inner diameter communicating with the passage 26 in the delivery guide 20, thereby providing a step down transition (not shown) between the first and second regions.

The relative sizes of the needle device 60 and delivery lumen may be configured such that the main portion 64 may be slidably received in the first region of the delivery lumen 69, 18c, and the tip portion 64 may be slidably received in the second region of the delivery lumen 69, 18c and the passage 26. In the retracted position, e.g., when the needle device 60 is initially loaded in the catheter 10, the transition 63 on the needle device 60 may be offset proximally from the step down transition within the delivery lumen 69, 18c by a predetermined distance. When the needle device 60 is actuated to deploy the tip 65, the step down transition may provide a stop to limit advancement of the needle tip 65 in the advanced position, e.g., allowing only a predetermined length of the tip 65 to be advanced from the outlet 29 of the delivery guide 20. In addition or alternatively, the actuator 54 on the catheter 10 (shown in FIG. 1) may limit the length of the tip 65 that is advanced from the outlet 29.

Such depth control may be particularly useful when injecting agent(s) into some tissue structures, e.g., into the epicardium, myocardium, and the like, without penetrating entirely into a chamber of the heart. Providing a stop close to the distal end 14 of the catheter 10 may provide improved depth control than the actuator 54, particularly if the catheter 10 (or the needle device 60) is capable of some axial compression or extension between the proximal and distal ends 12, 14.

Another potential advantage of having the main portion 62 larger than the tip portion 64 is that the lumen 66 of the needle device 60 may have a relatively larger diameter along most of the length of the needle device 60. If viscous fluids are delivered using the needle device 60, the resistance to flow may be lower in the main region 66a than in the tip region 66b of the lumen, thereby reducing the overall force needed to deliver the fluids, as compared to a uniform diameter lumen sized similar to the passage 26.

The needle device 60 may be formed from materials such that the needle shaft has a fixed length and sufficient column strength to prevent buckling, yet may be sufficiently flexible in bending, e.g., to facilitate navigation along a tortuous path if the catheter 10 is positioned along tortuous anatomy, without causing excessive friction and/or affecting the flexibility and torqueability profile of the catheter 10 for optimal navigability. In an exemplary embodiment, the tip portion 64 may have a relatively thin wall, e.g., no larger than 27 gauge, or no larger than 32 gauge, to reduce the rigidity of the tip portion 64, particularly within the passage 26 of the curved delivery guide 20. The main portion 62 may be constructed from a substantially flexible material, such as a braid reinforced polymeric shaft, single material polymer like polyimide, Nitinol, stainless steel, and the like, or alternatively, a semi-rigid or rigid material that can be selectively processed to reduce its stiffness in selected areas while maintaining general resistance to compression and extension. For example, the main portion may be formed by laser cutting a generally stiff tube with optimized relief cuts to impart desired flexibility (while maintaining the fluid-tight lumen 66).

Returning to FIG. 2, optionally, the needle device 60 may include a blocker wire 80, e.g., slidably received in the lumen 66. The blocker wire 80 may have sufficient length such that a tip 84 thereof extends a short distance beyond the needle tip 65 when fully advanced into the lumen 66, as shown. In this manner, the blocker wire 80 may provide a substantially atraumatic guide to facilitate advancing the needle device 60 into the catheter 10, e.g., minimizing the risk of the needle tip 65 catching on the wall of the delivery lumen 69, 18c and/or passage 26, which may otherwise remove material from the wall and/or dull or otherwise damage the needle tip 65. Once the needle device 60 is fully inserted into the catheter 10, the blocker wire 80 may be removed at any time before delivering agent(s) via the lumen 66. In an alternative embodiment, the needle device 60 may be provided to the user preloaded or the needle device 60 and/or may be integrally provided within the catheter 10, in which case the blocker wire 80 may be omitted, if desired.

Turning to FIG. 7, an exemplary method is shown for performing a medical procedure within the pericardial space 94, i.e., between a patient's heart 90 and the pericardial sac 92. Initially, the distal end 14 of the catheter 10 may be introduced into the patient's body, e.g., through the pericardial sac 92 into the pericardial space 94 with the balloon 30 in the contracted condition. For example, a distal end 7 of an introducer sheath 6 may be introduced into the patient's chest, e.g., using minimally invasive or open surgical access, and then the distal end 14 of the catheter 10 may be inserted through the sheath 6. The sheath 6 may at least partially straighten the delivery guide 20 and/or otherwise facilitate advancement of the distal end 14 into the pericardial space 94.

Once the distal end 14 is exposed within the pericardial space 94, the balloon 30 may be expanded and the catheter 10 may be manipulated to place the foot 28 and balloon 30 against the wall of the heart 90. For example, the catheter 10 may be rotated to orient the foot 28 towards heart 90, e.g., with the balloon 30 neutralizing any bias created by the curved shape of the delivery guide 20, as described elsewhere herein.

Figure 8:
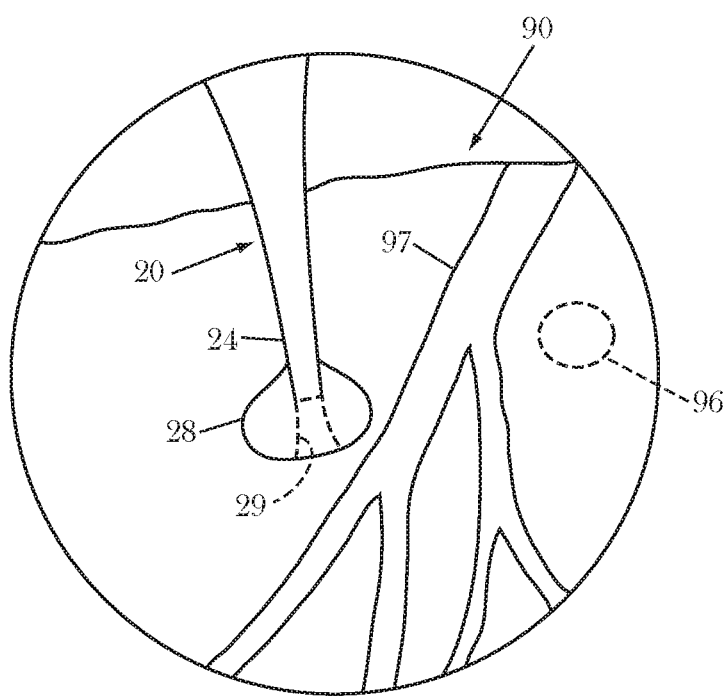
FIG. 8 is an exemplary image acquired using an imaging assembly of the system of FIG. 7.

The imaging assembly 40 may be used to acquire images of the pericardial space 94 and heart 90, e.g., as shown in FIG. 8. In addition, external imaging may be used, if desired in conjunction with acquiring images using the imaging assembly 40. The catheter 10 may be manipulated further as desired, e.g., to move the distal end 14 along the wall of the heart 90 until a target location is identified for treatment. For example, as shown, a target location 96 may be identified in the images for performing an injection while avoiding undesired anatomy such as an artery or vein 97. Once the foot 28 is positioned at the target location 96 (based on verification of the images), the needle device 60 may be activated to deploy the needle tip 65 from the outlet 29 and penetrate into the target location 97, as shown in FIG. 7.

In one method, the needle device 60 may be loaded into the catheter 10 immediately before activating the needle device 60, i.e., after positioning the foot 28 and outlet 29 at the target location 96. Alternatively, the needle device 60 may be loaded into the catheter 10 before the catheter 10 is inserted into the sheath 6 and remain in the retracted position during manipulation of the catheter 10. In either case, once the needle device 60 is fully received within the catheter 10, the tip 65 may be disposed within the delivery guide 20 adjacent the outlet 29. Optionally, the location of the tip 65 may be verified if the foot 28 and/or delivery guide 20 include a window that may be seen in the images of the imaging assembly 40 or may be verified directly outside the patient's body (if the needle device 60 is loaded before introduction). After the tip 65 is deployed and penetrated into the tissue at the target location 97, one or more agents may then be delivered through the needle device 60 into the tissue.

As described elsewhere herein, the depth of penetration of the needle tip 65 may be controlled by the mating stops in the distal section of the catheter 10 and/or by the actuator on the handle 50. For example, it may be desirable to inject one or more agents into the myocardium of the heart 90 while avoiding exposing the agent(s) within an underlying chamber 98 of the heart 90. Thus, a needle device 60 may be selected that has a predetermined length to ensure that the tip 65 extends from the outlet 29 of the foot 28 by a predetermined distance.

After the desired amount of the agent(s) is delivered, the needle tip 65 may then be retracted back into the delivery guide 20. Optionally, the catheter 10 may be manipulated further, e.g., to inject additional agent(s) at one or more additional locations within the epicardium/myocardium in a similar manner. If desired, the needle device 60 may be removed from the catheter 10 and replaced with a different needle device, e.g., having a different length, tip diameter, and/or other desired characteristics. Once the desired injections are completed, the balloon 30 may be deflated and the catheter 10 removed from the patient's body (along with the sheath 6 and/or any other devices).

Although particularly useful for performing injections via the pericardial space 94, the catheter 10 may be used to perform other procedures. For example, instead of the needle device 60, other devices may be introduced into the catheter 10 to deliver other therapies via the passage 26 of the delivery guide 20. For example, a laser device, an ablation device, and/or other device (not shown) may be positioned such that the device may be deployed from the outlet 29 and/or otherwise placed against tissue adjacent the outlet 29, whereupon energy or other treatments may be delivered.

Figure 9A:
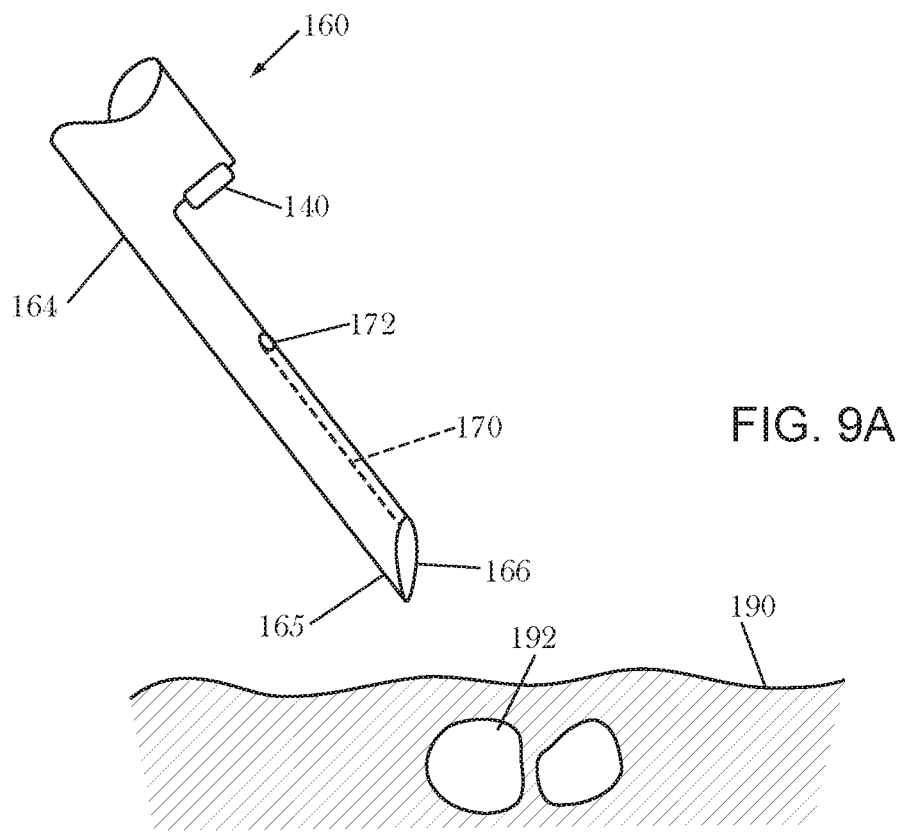
FIGS. 9A and 9B are side views of a distal portion of a needle device including a bleedback lumen and an imaging assembly.
Figure 9B:
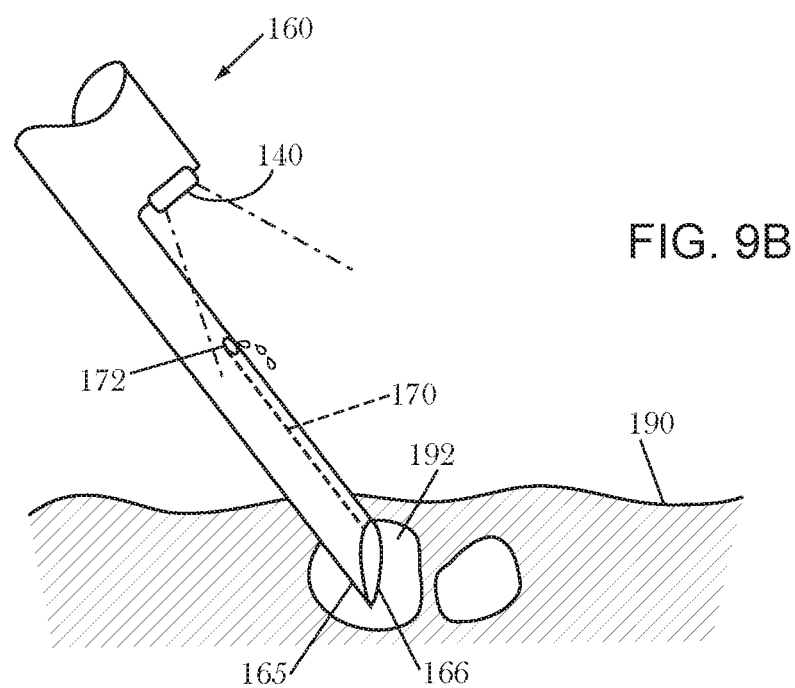

Turning to FIGS. 9A and 9B, another embodiment of a needle device 160 is shown that includes an elongate shaft terminating in a tip portion 164 including an imaging assembly 140 thereon, which may be similar to any of the embodiment described elsewhere herein. As shown, the tip portion 164 terminates in a beveled tip 165 defining an outlet 166. A relatively small bleedback lumen 170 may extend from the outlet 166 to a port 172 offset proximally from the outlet 166, e.g., within the field of the view of the imaging assembly 140.

Alternatively, the bleedback lumen 170 may be replaced with a groove or other feature that may cause blood to travel up from the outlet 166 to the port 172, e.g., due to capillary action and/or blood pressure encountered at the outlet 166. In a further alternative, the port 172 may be replaced with a window (not shown) that may enclose the bleedback lumen 170 yet allow blood passing the window to be identified in images from the imaging assembly 140. In yet another alternative, wicking material may be provided instead of the lumen 170 to draw blood along the tip 165 to a window to provide a visual indication when the tip 165 is positioned in a vessel.

For example, during use, the tip portion 164 of the needle device 160 may be positioned adjacent a tissue structure 190, e.g., the wall of a heart, into which an injection is to be made, as shown in FIG. 9A. In an exemplary embodiment, the needle device 160 may be loaded into a catheter, similar to the catheter 10 shown in FIG. 1 and described elsewhere herein, or other delivery sheath (not shown). Once positioned at a target location, the needle device 160 may be advanced to insert the tip 165 into tissue at the target location, as shown in FIG. 9B. If the tip 165 enters a blood vessel 192, blood may travel along the bleedback lumen 170 and exit the port 172. The imaging assembly 40 may be used to acquire images during insertion and identify whether such bleedback occurs, thereby confirming for the user whether the tip 165 is inserted into a vessel 192.

For example, it may be desirable to make a subcutaneous injection and avoid any vessels that may carry injected agents away from the target location. Alternatively, it may be desirable to deliver the agents into a target vessel. Either way, once the images are used to confirm the desired location of the tip 165, one or more agents may be delivered via the outlet 166.

Figure 10:
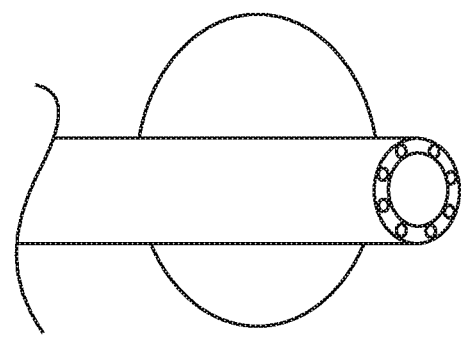
FIG. 10 is a side view of a distal region of another embodiment of an imaging catheter.

Turning to FIG. 10, another embodiment of an imaging catheter is shown that includes a large central lumen for delivery of one or more accessory devices (not shown). The catheter includes a balloon positioned proximal to the distal end, e.g., for creating space within a body cavity or potential space. The wall of the catheter include an imaging element and one or more illumination elements. The imaging element may comprise a coherent fiber bundle with a distal objective lens or may be constructed as described elsewhere herein. The Illumination elements may comprise one or more fiber optic elements or LEDs as described elsewhere herein.

Figure 11:
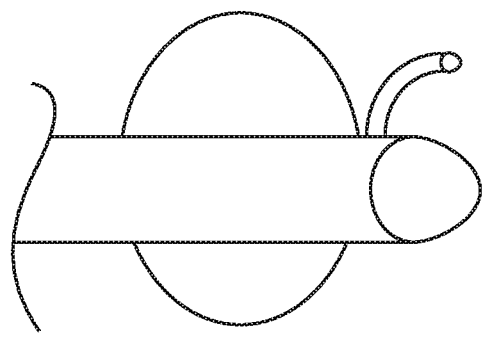
FIG. 11 is a side view of a distal region of yet another embodiment of an imaging catheter.

FIG. 11 shows a similar catheter including a large central lumen and balloon wherein the imaging element may be carried on a member extending away from the central axis of the catheter, e.g., to create distance and thereby field of view in order to image a device (not shown) introduced through the central lumen. Illumination elements are not shown but may be included as illustrated in FIG. 10 or elsewhere herein.

The foregoing disclosure of the exemplary embodiments has been presented for purposes of illustration and description. It is not intended to be exhaustive or to limit the invention to the precise forms disclosed. Many variations and modifications of the embodiments described herein will be apparent to one of ordinary skill in the art in light of the above disclosure.

Further, in describing representative embodiments, the specification may have presented the method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. An apparatus for imaging tissue during a medical procedure, comprising:

a tubular member comprising a tubular member proximal end, a tubular member distal end sized for introduction into a patient's body, a longitudinal axis extending between the tubular member proximal and distal ends, and one or more lumens extending between the proximal and distal ends;

a tubular extension comprising a tubular extension proximal end permanently attached to the tubular member distal end and a tubular extension distal end extending distally beyond the tubular member distal end to a tubular extension distal tip, the tubular extension having a cross-section smaller than the tubular member distal end and being biased to a curved shape, the tubular extension including a passage communicating from a first lumen of the tubular member to an outlet at the tubular extension distal tip;

a substantially atraumatic contact surface at the tubular extension distal tip having an area larger than the cross-section of the tubular extension for contacting tissue;

an imaging assembly on the tubular member distal end configured to acquire images of tissue adjacent the contact surface, a field of view of the imaging assembly is offset from the longitudinal axis such that the field of view is directed towards the contact surface when the tubular extension is in the curved shape;

a needle device disposed within the passage of the tubular extension; and an actuator on the proximal end of the tubular member for directing the needle device from a retracted position wherein a tip of the needle device is disposed within the passage and an advanced position wherein the tip of the needle device is deployed from the outlet at an angle relative to the longitudinal axis.

2. The apparatus of claim 1, further comprising a recess in the contact surface communicating with a vacuum source whereby vacuum may be applied to generate suction at to enhance engagement with contacted tissue.

3. The apparatus of claim 2, wherein the applied vacuum causes the tubular extension distal end to move in synchronization with movement with the contacted tissue.

4. The apparatus of claim 3, wherein the resulting field of view is relatively stationary with respect to the contacted tissue.

5. The apparatus of claim 1, wherein the imaging assembly comprises an imaging element mounted on the tubular member distal end such that the having a field of view is substantially centered on the contact surface when the tubular extension is in the curved shape.

6. The apparatus of claim 1, wherein the needle device comprises a tubular body that extends through the first lumen in the tubular member from the tubular member proximal end into the tubular member distal end and a tip portion that extends from the tubular body into the passage and terminates in the tip.

7. The apparatus of claim 6, wherein the needle device is removable entirely from the tubular member from the tubular member proximal end.

8. The apparatus of claim 6, wherein:
the first lumen has a first region defining a first inner diameter extending from the tubular member proximal end to a location within the tubular member distal end and a second region defining a second inner diameter smaller than the first inner diameter communicating with the passage in the tubular extension; and
the tubular body has a first portion extending from the tubular member proximal end into the tubular member distal end and sized to be slidably received in the first region of the first lumen, and a second portion sized to be slidably received in the second region of the first lumen and the passage,
wherein a transition from the first region to the second region provides a stop that engages a transition from the first portion to the second portion to limit advancement of the needle tip in the advanced position.

9. The apparatus of claim 1, further comprising a substantially transparent expandable member comprising a proximal end attached to the tubular member distal end and a distal end attached to the distal tip adjacent the contact surface such the imaging assembly is disposed within an interior of the expandable member.

10. The apparatus of claim 9, wherein the expandable member is expandable from a contracted condition to an enlarged condition when fluid is introduced through an inflation lumen of the tubular member into the interior of the expandable member.

11. A method for imaging tissue structures within a patient's body, comprising:
introducing a distal end of a catheter into a pericardial space adjacent a patient's heart;
expanding a balloon on the distal end wherein a curved delivery guide extends from the distal end of the catheter through an interior of the balloon, the delivery guide comprising a foot coupled to a distal surface of the balloon such that the foot is oriented transversely relative to the distal end;
manipulating the catheter such that a substantially atraumatic contact surface of the foot and the balloon contacts the epicardium of the heart; and
acquiring one or more images of the foot and adjacent tissue using an imaging assembly on the distal end to identify a target location within the epicardium, a field of view of the imaging assembly offset from a longitudinal axis of the catheter such that the field of view is directed towards the contact surface when the delivery guide is in a curved shape.

12. The method of claim 11, wherein the catheter is introduced into the pericardial space such that a longitudinal axis of the catheter is oriented along the wall of the heart and wherein the curved delivery guide is oriented orthogonal to the longitudinal axis to place the foot against the wall of the heart.

13. The method of claim 11, further comprising:
deploying a needle device from the delivery guide into the target location; and
delivering one or more agents via the needle device into the target location.

14. A method for imaging tissue structures within a patient's body, comprising:
introducing a distal end of a catheter into a pericardial space adjacent the patient's heart;
deploying a curved delivery guide extending from the distal end of the catheter such that the delivery guide adopts a curved shape and a substantially atraumatic contact surface on a distal tip the delivery guide is oriented transversely relative to the distal end;
manipulating the catheter such the contact surface contacts the heart wall; and
acquiring one or more images of the distal tip and adjacent tissue using an imaging assembly on the distal end to identify a target location on the heart wall, a field of view of the imaging assembly offset from a longitudinal axis of the catheter such that the field of view is directed towards the contact surface when the delivery guide is in the curved shape.

15. The method of claim 14, further comprising treating the target location using a device deployed from the delivery guide.

16. The method of claim 14, further comprising:
deploying a needle device from the delivery guide into the target location; and
delivering one or more agents via the needle device into the target location.

17. The method of claim 16, wherein an outlet in the contact surface is oriented substantially perpendicular to the longitudinal axis before deploying the needle device to direct a tip of the needle device into the epicardium of the heart.

18. The method of claim 14, wherein deploying the curved delivery guide comprises expanding a balloon on the distal end.

19. The method of claim 14, wherein the delivery guide is at partially straightened when the distal end is introduced into the pericardial space before being deployed.

20. The method of claim 19, wherein the delivery guide is straightened using a stylet inserted into the catheter before being introduced and wherein deploying the delivery guide comprises removing the stylet.

21. The method of claim 19, wherein introducing the distal end of the catheter comprises introducing the distal end through an introducer or sheath, the guide member at least partially straightened when the distal is introduced through the introducer or sheath, the guide member biased to resiliently return towards the curved shape when the distal end is deployed from the introducer or sheath.

* * * * *